United States Patent [19]

Stöcklin et al.

[11]  4,290,965
[45]  Sep. 22, 1981

[54] METHOD OF MAKING I[123] LABELED FATTY ACIDS

[75] Inventors: Gerhard Stöcklin, Jülich; Peter Laufer, Niederzier-Steinstrasse; Jürgen Machulla, Essen, all of Fed. Rep. of Germany

[73] Assignee: Kernforschungsanlage Jülich, Gesellschaft mit beschrankter Haftung, Jülich, Fed. Rep. of Germany

[21] Appl. No.: 136,928

[22] Filed: Apr. 3, 1980

[30] Foreign Application Priority Data

Apr. 7, 1979 [DE] Fed. Rep. of Germany ....... 2914089

[51] Int. Cl.$^3$ ................... C09F 7/00; C11C 3/00
[52] U.S. Cl. ................... 260/408; 562/602; 424/1
[58] Field of Search ........... 260/408; 424/1; 562/602

[56] References Cited

PUBLICATIONS

G. Stocklin, Int. J. Appl. Radiat. Isotopes 28 p. 131 (1977).
C. H. Freundlieb et al., Proceedings XV Int. An. Meeting of the Society of Nuclear Medicine, Groningen 9/13/77.
K. Vyska et al., Proceedings XVI Int. An. Meeting of the Society of Nuclear Medicine, Oct. 24–27, 1978, Madrid.
J. Machulla et al., J. Nuclear Med. 19, No. 3, 298–302 (1978).

Primary Examiner—John F. Niebling
Attorney, Agent, or Firm—Karl F. Ross

[57] ABSTRACT

A procedure for making $\omega$-I$^{123}$ labeled fatty acids in which the $\omega$-bromo-fatty acid is applied in a thin film or layer to a support and is there contacted in molten state with the I$^{123}$ iodide to effect halogen exchange.

5 Claims, No Drawings

METHOD OF MAKING $I^{123}$ LABELED FATTY ACIDS

BACKGROUND OF THE INVENTION

Fatty acids labeled with $I^{123}$, i.e. the radioactive isotope of iodine having a mass number of 123, which has a half-life of about 13 hours, in the $\omega$-position of the fatty acid molecule, are used as radiopharmaceuticals in diagnostic work with human and animal heart muscles and particularly for the localization of cardiac infarction and ischemia, to determine the deposition, obstruction and like processes involving fatty acids in the heart muscle, and hepatic exchanges as well as the metabolism of myocardial cells.

Reference may be made, in this regard, to the proceedings of the *Society of Experimental Biology and Medicine,* 148, pp. 215–218 (1975) and to CH. Freundlieb et al, *Proceedings, XV, Int. An. Meeting of the Society of Nuclear Medicine,* Groningen, September 13–16, 1977, and K Vyska et al, *Proceedings, XVI, Int. An. Meeting of the Society of Nuclear Medicine,* October 24–27, Madrid, 1978.

The iodine-123, with its half-life of 13 hours, is generally produced in a cyclotron and hence is both relatively expensive and comparatively shortlived so that the production of $I^{123}$ labeled compounds must be carried out as rapidly as possible, with maximum yield and with a minimum number of manipulations.

It has already been proposed to react radioactive iodine with $\omega$-bromo-fatty acids in a liquid phase, using as a reaction medium, a ketone in which the $\omega$-bromo-fatty acid is dissolved. The reaction is halogen replacement or exchange. The yields are less than 60% with a preparation time of 3 hours (see H.-J. Machulla et al, *J. Nuclear Med.* 19, No. 3, 298–302, 1978.) This relatively low yield and lengthy preparation time have restricted interest in this process.

G. Stöcklin, in a review article in *Int. J. Appl. Radiat. Isotopes,* 28, 1977, p. 131 ff., has indicated that $\alpha$-iodo-fatty acids can be made from $\omega$-bromo-fatty acids especially effectively by halogen exchange in a melt or fused form. The halogen exchange in the melt is carried out by adding the $\alpha$-bromo-fatty acid to the active iodide and forming the resulting mixture. This method has been found to require an excess of the $\alpha$-bromo-fatty acid or at least a large quantity thereof to pick up all of the residual iodide resulting from evaporation and bring it into effective contact with the fatty acid.

When one attempts to utilize this technique for the production of $\omega$-$I^{123}$ fatty acids, correspondingly satisfactory results are not obtained. In fact, the yield of the desired product is materially reduced because a decomposition reaction apparently competes with the exchange reaction which forms the $\omega$-$I^{123}$ fatty acid and some active iodine is lost by evaporation.

OBJECTS OF THE INVENTION

It is the principal object of the present invention to provide an improved method of making $\omega$-$I^{123}$ labeled fatty acids whereby disadvantages of earlier techniques can be avoided.

More specifically, it is an object of our invention to provide a process for reacting an $\omega$-bromo-fatty acid with a $I^{123}$ iodide which produces the corresponding $\omega$-$I^{123}$-fatty acid in comparatively high yields and with relatively short preparation times.

DESCRIPTION OF THE INVENTION

We have found that it is possible to obviate the disadvantages of the prior art systems mentioned previously and to obtain in a comparatively short time and in especially high yield, $\omega$-$I^{123}$ labeled fatty acids by reacting the corresponding $\omega$-bromo-fatty acid with an iodide in which the iodine is at least partly in the form of $I^{123}$ when the reaction is carried out between molten or fused $\omega$-bromo-fatty acid in a thin film or fine layer deposited upon an inert carrier with this layer being contacted with the $I^{123}$ iodide. Best results are obtained when the thickness of the layer is that of a monomolecular layer up to about 100 microns with the preferred layer thickness being between 0.05 microns to about 10 microns. Naturally the finer the layer (lower the thickness) the more rapidly will the film or layer react with the iodide.

Thus it is an essential feature of the invention to apply the $\omega$-bromo-fatty acid in a thin layer to the inert carrier.

Best results are obtained when the inert carrier is composed of glass and itself is subdivided into a comparatively small size, e.g. as glass beads, although the reaction can also be carried out on the walls of the reaction vessel.

According to a feature of the invention, a dilute solution of the $\omega$-bromo-fatty acid in a readily vaporizable solvent, is applied to the support and the solvent is evaporated thereon to leave a film of the $\omega$-bromo-fatty acid which is then contacted with the $I^{123}$ in the form of an iodide solution and the solvent thereof is vaporized.

Any volatile solvent for the $\omega$-bromo-fatty acid may be used provided that the solvent-vaporization conditions do not degrade the fatty acid or the support and we prefer to employ ketones such as acetones.

The support is advantageously glass beads having a smooth surface and of a diameter of 100 to 250 microns. Preferably the beads are spherical or substantially spherical.

The radioactive iodine is used in the form of a solution of the corresponding iodide to which a reducing agent is added such as a sulfite or hydrazine. The reaction occurs in a relatively short time and concurrent decomposition reactions are practically excluded.

The $\omega$-bromo-fatty acid can be used in units of say 5 to 10 mg, thereby yielding relataively small amounts of the $\omega$-$I^{123}$ labeled product so that a subsequent chromatographic separation can eliminate any starting materials from the labeled product. The use of small quantities of this nature also facilitates handling.

The reaction is preferably carried out at a temperature in the region of the melting point of the $\omega$-bromo-fatty acid for a period of 2 to 10 minutes.

While the invention is applicable to the labeling of any fatty acid, we have found it to be especially significant with long-chain $\omega$-bromo-fatty acids and especially the $C_{16}$ to $C_{18}$ fatty acids in the production of radiopharmaceuticals for the purposes described.

Thus the chromatographic separation can involve a high pressure liquid chromatography on silica gel with a nonpolar eluent in which polar components are dissolved or on silica gel with chemical bonded alkanes, silanes or alkylamines using polar protic liquids as the mobile phase or eluent.

As described in the latter application, moreover, the high purity $\omega$-$I^{123}$-fatty acid can be dissolved in so-called monomeric albumin, especially human serum albumin (HSA) with a molecular weight of about 67,000, and injected as with human serum albumin solutions.

SPECIFIC EXAMPLES

Example I

A 25 ml round bottom flack with NS10 ground glass joints and the like for connection to a suction pump is provided with 7 g of round glass beads with smooth surface and a particle size of 180 to 250 microns (60 to 80 mesh) with a capacity of 0.5%. A solution of 10 mg. of ω-bromo-heptadecanoic acid in 3 ml of acetone is poured over the glass beads and the solvent is slowly evaporated with evacuation of the flask.

The beads and the flask bottom, coated with the fine layer of ω-bromo-heptadecanoic acid is then contacted with practically carrier-free $I^{123}$ (about 50 mCi) in the form of sodium iodide dissolved in 1 ml of water which can be made somewhat alkaline with sodium hydroxide. The iodide solution also includes 2 ml of acetone and again the solvent is evaporated in vacuum.

Toward the end of the solvent evaporation, the flask is heated with a hot air blower to drive off traces of moisture.

The closed flask is then heated in an oil bath at a temperature of 80° C. to melt the fatty acid over a period of 10 minutes and to effect the reaction.

The reaction mixture in the flask is then dissolved 3 times in 3 ml. of an eluent consisting of 2.5% by volume glacial acetic acid, in n-heptane, and the collected solution is subjected to high pressure liquid chromatography. The separating column is a tube 30 cm long and 1 cm inner diameter, packed with silica gel with particle size of about 10 microns. The eluent is the same solvent and the flow rate is 5 ml/min. The ω-$I^{123}$-heptadecanoic acid is recovered in 30 minutes in pure form and by evaporation of the eluent.

Example II

A solution of 10 mg of 17-bromo-heptadecanoic acid in 2 ml of acetone is evaporated to dryness in a 25 ml flask and 1 ml of aqueous $I^{123}$ iodide solution containing 10 microliters of 25% hydrazine solution, is added. Evaporation to dryness is followed by a heating of the residue to 150° C., whereupon the reaction mass is dissolved in the above-mentioned eluent and subjected to high pressure liquid chromatography as described above. The time required is 45 minutes and the yield was 75%.

Example III

The procedure of Example I was carried out with ω-bromo-hexadecanoic acid and the corresponding ω-$I^{123}$ hexadecanoic acid was obtained with corresponding yield in high purity. The same applies to ω-bromo-octadecanoic acid.

We claim:

1. A method of making a ω-$I^{123}$ labeled fatty acid which comprises the steps of:
   (a) applying a thin layer of an ω-bromo-fatty acid to an inert support;
   (b) contacting said layer on said support with an $I^{123}$ containing iodide; and
   (c) heating said layer on said support in contact with said $I^{123}$ iodide to a temperature sufficient to effect halogen substitution whereby said ω-bromo-fatty acid is converted into the corresponding ω-$I^{123}$-fatty acid.

2. The method defined in claim 1 wherein the reaction in step (c) is carried out for a period of 2 to about 10 minutes.

3. The method defined in claim 2 wherein said ω-bromo-fatty acid is a $C_{16}$ to $C_{18}$ fatty acid.

4. The method defined in claim 3, further comprising the step of dissolving the product of the reaction in step (c) directly from said support and subjecting the resulting solution to chromatography to recover said ω-$I^{123}$-fatty acid.

5. The method defined in claim 1, claim 2, claim 3 or claim 4, wherein the reaction product formed in step (c) is subjected to high-pressure liquid chromatography by dissolving the reaction product in the eluent and passing same through a high-pressure liquid chromatography column, said column consisting of silica gel which is eluted with a nonpolar eluent containing a dissolved polar component, or silica gel to which an alkane or an alkylamine is bonded and which is eluted with a polar protic eluent.

* * * * *